US00PP19762P2

(12) United States Plant Patent
White

(10) Patent No.: US PP19,762 P2
(45) Date of Patent: Feb. 24, 2009

(54) APPLE TREE NAMED 'PREMA280'

(50) Latin Name: *Matus domestica*
Varietal Denomination: PremA280

(75) Inventor: Allan G. White, Havelock North (NZ)

(73) Assignee: Prevar Limited, Hastings (NZ)

( * ) Notice: Subject to any disclaimer, the term of this patent is extended or adjusted under 35 U.S.C. 154(b) by 68 days.

(21) Appl. No.: 11/436,106

(22) Filed: May 16, 2006

Related U.S. Application Data

(60) Provisional application No. 60/682,206, filed on May 17, 2005.

(51) Int. Cl.
*A01H 5/00* (2006.01)

(52) U.S. Cl. ..... Plt./161

(58) Field of Classification Search ..... Plt./161
See application file for complete search history.

(56) References Cited

U.S. PATENT DOCUMENTS

PP13,888 P3 * 6/2003 White ..... Plt./161

OTHER PUBLICATIONS http://www.prevar.co.nz/what–we–do/commercial–releases/sweetie–prem1a/*
UPOV–ROM GTITM Plant Variety Database 2008/02 search for cultivar Prem1A.*

* cited by examiner

*Primary Examiner*—Annette H Para
(74) *Attorney, Agent, or Firm*—Stratton Ballew PLLC

(57) ABSTRACT

'PremA280' is a moderately vigorous 'Gala' type apple cultivar distinguished by its dark red fruit. The fruit of 'PremA280' matures a few days before 'Royal Gala' and is notable for its sweet flavor and crisp texture.

1 Drawing Sheet

Latin name of the genus and species of the plant claimed: *Malus domestica.*
Variety denomination: 'PremA280'.

BACKGROUND OF THE INVENTION

'PremA280' was selected from a population of seedlings derived from crossing 'Braeburn' (not patented)×'Royal Gala' (U.S. Plant Pat. No. 4,121). The cross was made at Hawkes Bay, New Zealand. 'PremA280' has been asexually propagated, and has been shown to remain true to type over successive generations.

BRIEF SUMMARY OF THE INVENTION

'PremA280' is distinguishable from its parents and from other known varieties by a number of characteristics, as set forth in Table 1 below.

TABLE 1

| | 'PremA280' | 'Royal Gala' | 'Braeburn' | 'Scifresh' |
|---|---|---|---|---|
| Bloom time | Mid to Late season | Late | Mid-season | Mid-season |
| Fruit Shape | Conical | Globose | Globose conical | Globose conical |
| Fruit Overcolor | Dark red | Bright red | Red | Red |
| Harvest Maturity | Early to mid-season | Early to mid-season | Late | Late |

In particular, 'PremA280' is distinguished by its dark red fruit, early maturity and sweet, crisp fruit.

BRIEF DESCRIPTION OF THE PHOTOGRAPH

The photograph shows the fruit, leaves, and branches of 'PremA280'.

DETAILED BOTANICAL DESCRIPTION

The following is a detailed botanical description of 'PremA280,' a new and distinct cultivar of *Malus domestica.* The description is based on observations of 2 year old trees planted at Parker, Wash., as well as observations of fruit harvested from trees planted at Hawkes Bay and Nelson, New Zealand. It should be understood that the botanical and analytical characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Tree: Habit — spreading; branch angle — 60° to 90°, moderately vigorous (compare to 'Royal Gala'); height — 1.8 m; spread — 1.2 m.

Trunk: Diameter 2.4 cm at 20 cm above the ground; bark smooth, grey 201D; Lenticels — approximately 16 per square inch, elongated, greyed yellow 160D.

Branches: (Primary lateral branch 90 cm above the ground) Length 76 cm; diameter 0.4 cm; crotch angle 80°, grey 201A; Lenticels — approximately 10 per square inch, elongated, greyed yellow 160D.

Winter hardiness: Hardy in area tested.

Flowering: Mid to late season; first bloom April 17, full bloom April 22 (2008 growing season, Parker, Wash.).

Bud: 5 per spur; compact; elongated; length 1 cm, diameter 0.7 cm; red-purple 63A.

Balloon stage: Length 2.5 cm, diameter 1.0 cm; red-purple 63C.

Flower: Size — diameter 4.6 cm, depth 1.4 cm; 5 per cluster; Petals — 5 per flower, not touching, length 1.8 cm, width 1.4 cm, apex rounded, base equilateral, margin smooth, upper surface white N155B, lower surface red-purple 62A when fully open; Sepals — 5 per flower, pointed length 1.0 cm, width 0.5 cm, yellow-green 144A; Pedicel — length 2.8 cm, diameter 0.1 cm, yellow-green 144A; Pistil — Length 1.3 cm, width 0.8 cm, yellow-green 144A; Anthers — 15 per flower, length 0.2 cm, pollen yellow 1C; Stigma — length 0.1 cm, yellow 1C; Style — length 0.5 cm, yellow 1C; Ovary — length 0.9 cm, width 0.1 cm, color yellow-green 144A.

Pollenization requirements: Cross pollenization required; any diploid apple tree blooming during the same period is a suitable pollenizer.

Leaf: Attitude in relation to shoot — 75°; Length 8.0 cm, width 4.5 cm; margin serrated; upper surface green 137A, lower surface green 146C; Petiole — length 2.0 cm, diameter 0.4 cm, green 153D.

Fruit: Shape — conical; Skin — thick, ground color yellow 154B, over color dark red 179A, percent over color 60 to 100%, over color pattern striped, lenticels inconspicuous; Russeting — none; Flesh — cream 155B, moderately firm, crisp, not gritty, very juicy, sweet, medium acidity, rich aroma, not bitter or astringent; Eating quality and appearance — very good.

Productivity: Similar to 'Royal Gala'.

Disease/insect resistance/susceptibility: None noted.

We claim:

1. A new and distinct apple tree, substantially as shown and described herein.

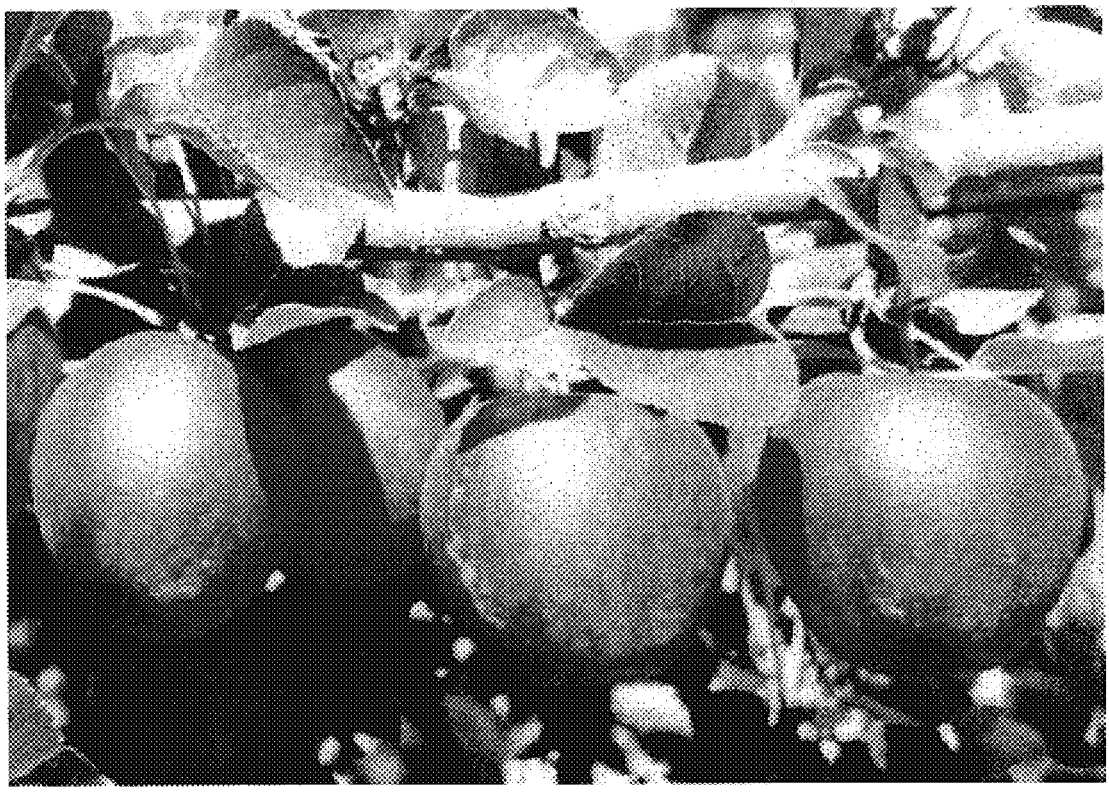

* * * * *